US006938465B2

United States Patent
Goto (10) Patent No.: US 6,938,465 B2
(45) Date of Patent: Sep. 6, 2005

(54) METHOD OF RATING BRITTLENESS OF COATING SUBSTANCE AND DEVICE FOR IMPLEMENTING THE BRITTLENESS RATING METHOD

(75) Inventor: Yasutomo Goto, Fujinomiya (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/657,127

(22) Filed: Sep. 9, 2003

(65) Prior Publication Data

US 2004/0045357 A1 Mar. 11, 2004

(30) Foreign Application Priority Data

Sep. 11, 2002 (JP) .......................................... 2002-265199

(51) Int. Cl.[7] .............................................. G01N 29/04
(52) U.S. Cl. ................................................ 73/87; 73/801
(58) Field of Search .......................... 73/87, 801, 587, 73/589, 597, 598, 599, 600, 602, 1.04, 666, 866, 588

(56) References Cited

U.S. PATENT DOCUMENTS

| | | | | |
|---|---|---|---|---|
| 2,186,014 A | * | 1/1940 | Ellis ............................ 73/104 |
| 3,791,198 A | * | 2/1974 | Alburger ...................... 73/1.04 |
| 4,610,157 A | * | 9/1986 | Vicki et al. ................... 73/1.04 |
| 4,696,191 A | * | 9/1987 | Claytor et al. ................ 73/600 |
| 4,856,326 A | * | 8/1989 | Tsukamoto ................. 73/150 A |
| 5,170,366 A | * | 12/1992 | Passarelli ...................... 702/41 |
| 5,209,119 A | * | 5/1993 | Polla et al. .................... 73/723 |
| 5,260,024 A | * | 11/1993 | Aspden et al. ................. 422/53 |
| 5,319,977 A | * | 6/1994 | Quate et al. ................... 73/606 |
| 6,076,411 A | * | 6/2000 | Horvath ........................ 73/866 |
| 6,270,817 B1 | * | 8/2001 | Barnes et al. .................. 426/92 |
| 6,311,538 B1 | * | 11/2001 | Martin ......................... 73/1.04 |
| 6,799,472 B2 | * | 10/2004 | Nakayama et al. ............ 73/827 |
| 2004/0079147 A1 | * | 4/2004 | Maenpaa | |

* cited by examiner

Primary Examiner—Hezron Williams
Assistant Examiner—Jacques M. Saint-Surin
(74) Attorney, Agent, or Firm—Young & Thompson (57) ABSTRACT

Brittleness of a coating substance such as a coating film that is too brittle and/or too thin to be independently removed or handled is rated on the basis of an outcome of detection of acoustic emissions which are produced when a test film piece prepared by laminating a support with the coating substance is deformed by a compression transverse test device and detected by an AE sensor attached to the test film.

16 Claims, 5 Drawing Sheets

METHOD OF RATING BRITTLENESS OF COATING SUBSTANCE AND DEVICE FOR IMPLEMENTING THE BRITTLENESS RATING METHOD

BACGROUND OF THE INVENTION

1. Field of the Invention

The present invention relates to a brittleness rating method of rating brittleness of coating substances and a device for performing the brittleness rating method and, more particularly, to a brittleness rating method of rating brittleness of coating substances through use of the detection result of acoustic emissions and a device for performing the brittleness rating method.

2. Description of Related Art

There have been widely used various methods of rating strength or brittleness of films or coatings. Fracture toughness test methods provided in JIS (Japanese Industrial Standard) K-6911 that are applied to tests on metals and thermosetting plastics are often used to rate strength or brittleness of test pieces such as a test film piece. Of these test methods, Charpy impact test method, Izod impact test method and three-point bending test methods impose restraints on test film pieces. That is, the test film piece has to be thicker than approximately 2 mm and has to have crazing beforehand.

Brittleness rating methods, for example such as provided in JIS K5400, can be utilized to rate or evaluate elasticity or flexibility, Erichsen values and/or impact load carrying capacity of test film pieces. In such a brittleness rating method, brittleness of a test film piece is visually rated according to a diameter of one of cores different in diameter in 10 mm increments in a range from 10 mm to 50 mm at which the test film piece wound around thereon causes crazing. In addition, bending test machines such as manufactured by SUGA Testing Machine Co., Ltd. can be used to rate or evaluate brittleness of test film pieces. With such a bending test machine, brittleness of a test film piece is visually evaluated according to a curvature of a core continuously varying in curvature at which a test film piece causes crazing when the test film piece is put in contact with the core. Further details regarding the brittleness rating or evaluation method using the bending test can be arrived at by referring "Solid State Properties And Evaluation Methods Of Coating Films" by Takeyuki Tanaka, page 242, published 1993 by Rikou Shuppan Co., Ltd.

However, in the test method provided in JIS K-6911, when making measurement of flexural strength or elasticity modulus of test pieces are made by applying an external load to a test piece, it is difficult to detect a change in the external load at an occurrence of fracture of the test piece with sufficient sensitivity if the test piece is thin and brittle. Additionally, a test piece possibly breaks resulting simply from formation of crazing if the test film piece is thinner than, for example, 0.1 mm and brittle. In consequence, the fracture toughness test method is not always really suited to measurement of brittleness of coating substances such as an image receiving coating film for use in electro photography that is too brittle and/or or too thin to be independently removed and/or handled in the form of film.

On the other hand, in the brittleness evaluation method provided in JIS K5400, it is difficult for viewers or examiners to determine a momentary occurrence of crazing or delamination of a test film piece precisely because of visual examination and, in consequence, it is hard to rate brittleness with high accuracy.

SUMMARY OF THE INVENTION

It is therefore an object of the present invention to provide a brittleness rating method of rating brittleness of test film pieces with high precision even though the test film pieces are too brittle to be independently removed and/or handled in the form of film.

It is another object of the present invention to provide a device of performing a high-precision brittleness rating method.

The aforesaid objects of the present invention are accomplished by a brittleness rating method comprising the steps of causing a test film piece formed by laminating a support with a coating substance, e.g. a coating film such as an electrophotographic image receiving film, to produce deformation, detecting acoustic emissions that the coating substance produces resulting from said deformation of the test film piece, and rating brittleness of said coating substance on the basis of a detected outcome of acoustic emissions.

According to the brittleness rating method of the present invention, because the coating substance is deformed in the form of lamination on the support and brittleness of the coating substance is rated on the basis of acoustic emissions that the coating substance produces, the brittleness rating of coating substance is performed with high precision even though the coating substance is too brittle to be independently removed and/or handled in the form of film.

Furthermore, deformation of the test film piece is caused preferably using a compression transverse test device that applies an external load to the middle of the test film piece supported at opposite sides thereof by two wedges apart from each other in a transverse direction of the test film piece. The compression transverse test device preferably applies an external load to the test film piece with a compression head that descends at a constant speed keeping in contact with the test film piece. In this instance, a descent distance of the compression head can be easily represented by time, and, in consequence, deformation of the test film piece is easily quantified correspondingly to time. The utilization of the compression transverse test device makes it easy to cause desired deformation of the test film piece.

Acoustic emissions from the coating film may be easily detected by means of an acoustic emission sensor attached to the test film piece. The acoustic emission sensor is known in various forms and may take any form well known to those in the art.

When the brittleness rating method is applied to determination as to whether a coating substance is qualified for an electrophotographic image receiving film, the coating substance is determined as qualified for the electrophotographic image receiving film when a distance of descent of the compression head is greater than 2 mm at detection of a first acoustic emission in the event that the test film piece is supported at opposite sides apart from each other at a distance of 50 mm in a transverse direction of the test film piece. Accordingly, when sorting coating substances that satisfy the rating standard that the distance of descent of the compression head at detection of a first acoustic emission is greater than 2 mm, the coating support is qualified to have brittleness suitable for a reliable and quality electrophotographic image receiving film without being subjected to any bending test.

A device for implementing the brittleness rating method of the present invention comprises deforming mans for causing deformation of the test film piece, such as a compressive transverse test device, which supports the test film piece at opposite sides apart from each other in a transverse direction of the test film piece by applying an external load to the test film piece at a middle between the opposite sides, acoustic emission detecting means, such as an acoustic emission sensor, for detecting acoustic emissions that the coating substance produces resulting from deformation of the test film piece, the acoustic emission detecting means being detachably attached to the test film piece, and rating means for rating brittleness of the coating substance on the basis of an output from the acoustic emission detecting means.

According to the brittleness rating method of the present invention, because the coating substance in the form of lamination on the support is deformed and brittleness of the coating substance is rated on the basis of acoustic emissions that the coating substance produces, the rating of brittleness of the coating substance can be performed with high precision even though the coating substance is too brittle to be independently removed and/or handled in the form of film.

BRIEF DESCRIPTION OF THE DRAWINGS

The above and other objects and features of the present invention will be clearly understood from the following detailed description when read with reference to the accompanying drawings, in which.

DETAILED DESCRIPTION OF THE PREFERRED EMBODIMENTS

Figure 1:
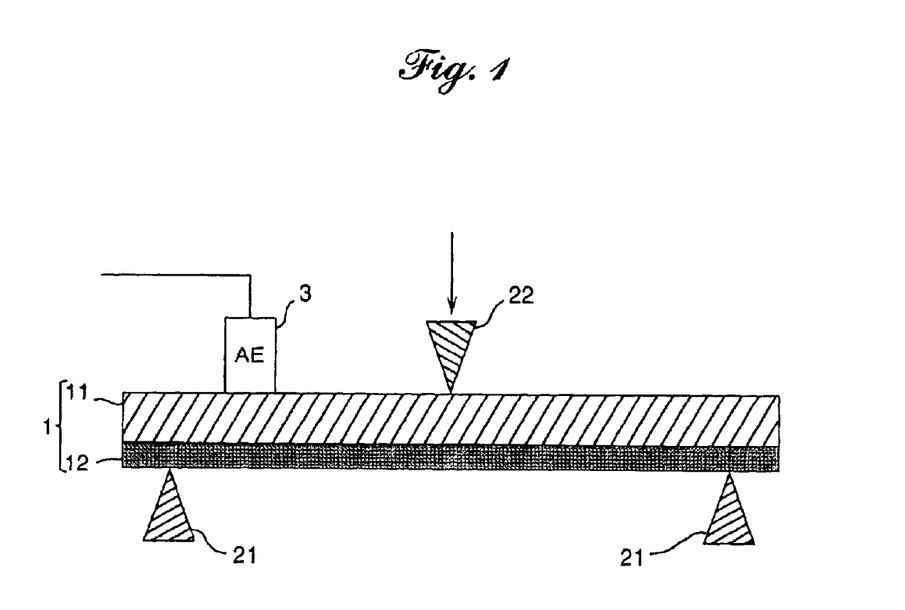
FIG. 1 is a schematic view showing a fundamental manner of rating brittleness of coating substances such as coating films according to the present invention.

Referring to the drawings in detail and, in particular, to FIG. 1 showing a fundamental manner of rating brittleness of coating substances such as coating films according to the present invention, the rating of brittleness is made using a test film piece 1 that is prepared by laminating a support 1 with a coating substance in the form of a film 12, that is an object for brittleness rating, in the form of a film. The use of this type of test film piece 1 enables high-precision brittleness rating of coating supports, e.g. a thin coating film of an electrophotographic image receiving material, etc., that are too brittle to be independently removed and/or handled. The support 11 is desirably made of a polyethylene telephthalate (PET) film or a paper sheet laminated with a polyolefin resin. It is desirable that the support 11 is higher in strength than the coating film 12. Lamination of the coating film 12 over the support 11 is performed by a wire coater or the like so as to have a thickness appropriate to the type of substances and the intended purpose of brittleness rating.

An acoustic emission (AE) sensor 3 is attached to the test film piece 1, desirably to the support 11. Otherwise, the AE sensor 3 may be attached to the test film piece 1 keeping in contact with the coating film 12 or to any part of the test film piece 1 where the AE sensor 3 is allowed to operate with high sensitivity. It is preferred to apply a couplant such as a glycerin paste to an interface between the AE sensor 3 and the test film piece 1. The acoustic emission sensor 3 is known in various forms and may take any form well known in the art and available commercially.

The test film piece 1 with the AE sensor 3 attached thereto is set in a deforming device such as a compression transverse test device that is schematically shown by two wedge-shaped supporting props 21 and one compression head 22. Specifically, the test film piece 1 with the coating film 12 faced down is put on the supporting props 21 and is applied with an external compression load by the compression head 22 so as thereby to be concavely curved downward. It is preferred to determine the distance between the supporting props 21 according to the detection sensitivity of the AE sensor 3 and the intended purpose of brittleness rating. The test film piece 1 is put on the supporting props 21 so that the coating film 12 faces either downward or upward. Further, although the support props 21 and the compression head 22 are shown as having a wedge-shaped cross-section, they may take any suitable shapes in cross-section, in particular any edge-shaped cross-section, according to intended purposes of the brittleness rating and objects of the brittles rating.

The AE sensor 3 catches acoustic emission waves (AE waves) which the coating film 12 produces resulting from deformation of the test film piece 1. For desirable detection of acoustic emission waves, the AE sensor 3 converts AE waves propagating in and along the surface of the test film piece 1 into electric signals (AE signals). Since the AE signals are feeble, the AE signals are amplified by a preamplifier (not shown). Subsequently, the AE signals pass through a band-pass filter (not shown) to filter out noises other than the AE waves. It is preferred to separate a substantive part of the AE signals that are higher in level than a predetermined discrimination threshold level through a discriminator (not shown). The degree of amplification, the range of band-pass filter and the threshold level for discrimination are determined preferably according to intended purposes of the brittleness rating and objects of the brittles rating. The brittleness of coating substance is rated based on measurements of acoustic emissions. The brittleness can be quantified according to compressive stress, compressive strain, stress-strain curve, destructive energy due to pressure or curvature radius upon detection of acoustic emissions, or various numerical values obtained from these attributes. It is preferred to rate quantified brittleness of coating substances according to types of coating substances and intended purposes of the brittleness rating.

The brittleness rating may be humanly achieved, or otherwise may be achieved through a computer. In the case of performing computer-aided brittleness rating, it is preferred to express one or more of these attributes at detection of acoustic emissions numerically and calculate various values from the numerical values. Further, it is preferred to specify a standard value for an assessment of a coating substance based on measurements of acoustic emissions and the calculated numerical values.

Figure 2:
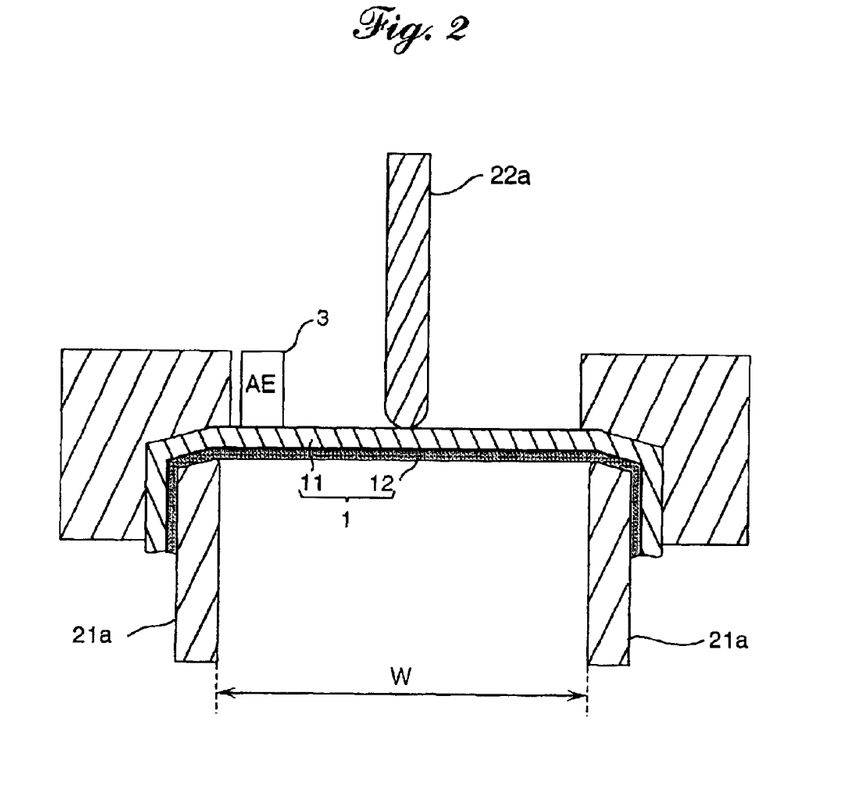
FIG. 2 is a cross-sectional view of a brittleness rating device according to an embodiment of the present invention.

FIG. 2 shows a brittleness rating device according to an embodiment of the present invention. In the following embodiment, various test film pieces 1 were prepared for brittleness rating. Each test film piece 1 measured 150 mm length and 25 mm width. The coating film 12 was formed on the support 11 by means of a wire coater and dried so as to have a uniform spread of 15 g/m$^2$ after drying. A compression transverse test device for tensilon (which was standardized according to JIS K6911 and manufactured by Orientec Co., Ltd.) was used as the deforming device for causing deformation of the test film piece 1. The compression transverse test device was adjusted so that supporting props 21a were at a transverse distance of 50 mm. The test film piece 1 was put on the support props 21a so that the coating film 12 faced downward as shown in FIG. 2. The AE sensor 3 was fixedly attached to the test film piece 1 by a mylar tape. In this instance, a glycerin paste was applied as a couplant to an interface between the AE sensor 3 and the support 11.

Detection of acoustic emissions was continued for 200 seconds while deforming the test film piece 1 by forcing the compression head 22a to descend at a descending speed of 1 mm/min keeping in contact with a center area of the test film piece 1. AE signals provided by the AE sensor 3 were sorted with a discrimination level of 52 dB and analyzed using an AE analytical equipment such as 9502 U-PLOT (manufactured by NF Electronic Instruments). The AE signals thus sorted were directed to a graphic plotter (e.g. 7550A Graphic Plotter manufactured by Hewlett-Packard Co.) through a GP-IB (general protocol-interface bus).

EXAMPLE I

A test film piece 1 was prepared by applying a dispersion liquid of coating substance to a support 11 made of a polyethylene telephthalate (PET) film 100 μm in thickness to form a lamination of a coating film 12 on the support 11. The dispersion liquid was prepared by dispersing 30 g of a polyester resin (KZA-1449 commercially distributed by Unitika Ltd.) in 100 g of water. The result of measurements of acoustic emissions regarding the test film piece 1 is graphically demonstrated in a chart shown in FIG. 3 in which the ordinate and abscissa axes represent AE count and time (second), respectively.

Figure 3:
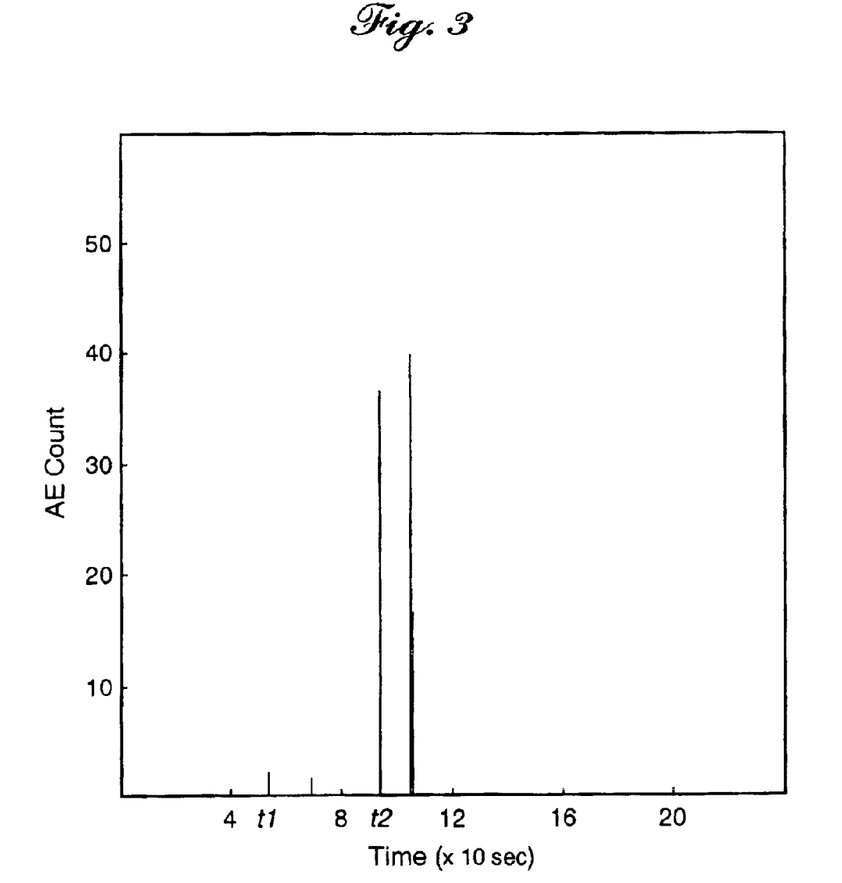
FIG. 3 is a graphic diagram showing measurements of acoustic emissions that a coating substance produces when a test film piece of example I is deformed.

The compression head 22a descends at a constant speed to deform the test film piece 1, so that the time scale represents the distance of descent of the depression head 22a, and hence, quantitative deformation of the test film piece 1. The starting point of measurement is the moment at which the compression head 22a is just brought into contact with the test film piece 1 without applying any compressive load to the test film piece 1, in other words, the moment at which the distance of descent of the compression head 22a is 0 (zero) from a position where the compression head 22a is in contact with the test film piece 1. Therefore, brittleness of the coating film 12 may be quantitatively rated according to deformation of the test film piece 1 at an occurrence of a first acoustic emission. In this instance, as shown in FIG. 3, as a first AE count appears at a time t1 in the 50 sec. range, the brittleness of the coating film 12 is rated on the basis of the time t1. Alternatively, the brittleness of the coating film 12 may be rated on the basis of a time at which an AE count greater than a threshold count of, for example, 30 appears. In this instance, as a first AE count exceeding the threshold count of 30 appears at a time t2 in the 90 sec. range as shown in FIG. 3, the brittleness of the coating film 12 is rated on the basis of the time t2.

EXAMPLE II

A test film piece 1 was prepared by applying a dispersion liquid of coating substance to a support 11 made of a paper sheet 100 μm in thickness that was laminated with a polyolefin resin to form a lamination of a coating film 12 on the support 11. The dispersion liquid was prepared by dispersing 400 g of a polyester resin (Tafton® U-5 commercially distributed by Kao Corporation) in 800 g of methyl ethyl ketone. The result of measurements of acoustic emissions of the test film piece 1 is graphically demonstrated in the chart shown in FIG. 4 in which the ordinate and abscissa axes represent AE count and time (second), respectively.

Figure 4:
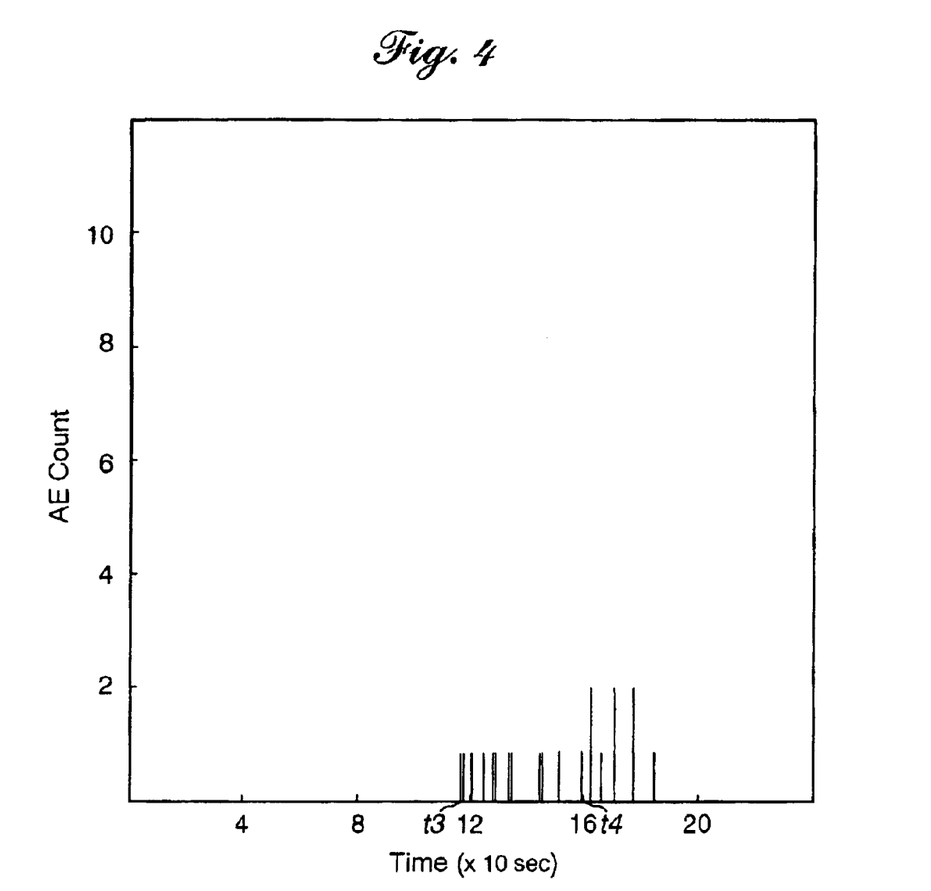
FIG. 4 is a graphic diagram showing measurements of acoustic emissions that a coating substance produces when a test film piece of example II is deformed.

In this instance, as a first AE count appears at a time t3 in the 110 sec. range, the brittleness of the coating film 12 may rated on the basis of the time. Alternatively, the brittleness of the coating film 12 may be quantitatively rated on the basis of a time at which an AE count greater than a threshold count of, for example, 2 appears. In this instance, as a first AE count exceeding the threshold count of 2 appears at a time t4 in the 160 sec. range, the brittleness of the coating film 12 may be rated on the basis of the time t4.

EXAMPLE III

A test film piece 1 was prepared by applying a dispersion liquid of coating substance to a support 11 made of a paper sheet 100 μm in thickness that was laminated with a polyolefin resin to form a lamination of a coating film 12 on the support 11. The dispersion liquid was prepared by dispersing 400 g of a polyester resin in 800 g of methyl ethyl ketone. The polyester resin was a polymer of a telephthalic acid and ethylene oxide modified bisphenol A that has a number average molecular weight of 5000 and a glass transition temperature (Tg) of 65° C. The result of measurements of acoustic emissions of the test film piece 1 is graphically demonstrated in the chart shown in FIG. 5 in which the ordinate and abscissa axes represent the umber of acoustic emissions and time (second), respectively.

Figure 5:
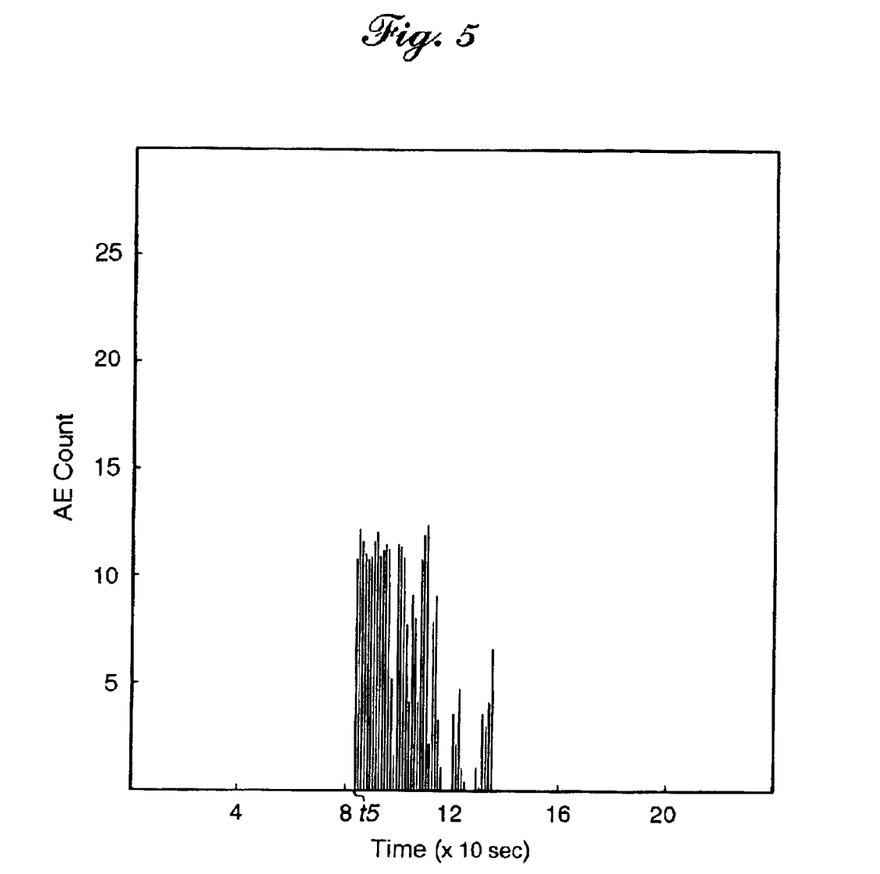
FIG. 5 is a graphic diagram showing measurements of acoustic emissions that a coating substance produces when a test film piece of example III is deformed.

In this instance, as a first AE count appears at a time t5 in the 80 sec. range, the brittleness of the coating film 12 may be rated on the basis of the time t5.

Test film pieces 1 were further prepared as examples IV~IX and brittleness of these test film pieces 1 were rated under the same condition as applied to those of example I~III. In addition, brittleness of the test film pieces 1 of examples IV~IX were rated on the basis of an occurrence of crazing due resulting from bending (flexural crazing) test and an occurrence of crazing resulting from that the test film piece 1 was left as it was for two weeks (spontaneous crazing). The bending test was made by winding the test film piece 1 around a core with a diameter of 50 mm and unwinding it immediately thereafter. Then, the test film piece 1 was visually examined to determine whether the test film piece 1 produced crazing. The result of visual examination of the test film pieces 1 of examples IV~IX is demonstrated in Table I.

EXAMPLE IV

A test film piece 1 was prepared by applying a dispersion liquid of coating substance to a support 11 made of a paper sheet 100 μm in thickness that was laminated with a polyolefin resin to form a lamination of a coating film 12 on the support 11. The dispersion liquid was prepared by dispersing 400 g of a polyester resin (Tafton® U-5 commercially distributed by Kao Corporation), 60 g of titanium dioxide (Taipek® A-220 commercially distributed by Ishihara Sangyo Co., Ltd.) and 34.8 g of triphenyl phosphin (TPP) (Daihachi Chemical Co., Ltd.) in 800 g of methyl ethyl ketone. The triphenyl phosphin (TPP) was used as a plasticizer.

EXAMPLE V

A test film piece 1 was prepared by applying a dispersion liquid of coating substance to a support 11 made of a paper sheet 100 μm in thickness that was laminated with a polyolefin resin to form a lamination of a coating film 12 on the support 11. The dispersion liquid was prepared by dispersing 400 g of a polyester resin (Vyron® 200 commercially distributed by Toyobo Co., Ltd.) and 60 g of titanium dioxide (Taipek® A-220 commercially distributed by Ishihara Sangyo Co., Ltd.) in 800 g of methyl ethyl ketone.

EXAMPLE VI

A test film piece 1 was prepared by applying a dispersion liquid of coating substance to a support 11 made of a paper sheet 100 μm in thickness that was laminated with a polyolefin resin to form a lamination of a coating film 12 on the support 11. The dispersion liquid was prepared by dispersing 400 g of a polyester resin (KZA-1449 commercially distributed by Toyobo Co., Ltd.) and 60 g of titanium dioxide (Taipek® A-220 commercially distributed by Ishihara Sangyo Co., Ltd.) in 800 g of methyl ethyl ketone.

EXAMPLE VII

A test film piece 1 was prepared by applying a dispersion liquid of coating substance to a support 11 made of a paper sheet 100 μm in thickness that was laminated with a polyolefin resin to form a lamination of a coating film 12 on the support 11. The dispersion liquid was prepared by dispersing 400 g of polyester resin (Tafton® U-5 commercially distributed by Kao Corporation) and 60 g of titanium dioxide (Taipek® A-220 commercially distributed by Ishihara Sangyo Co., Ltd.) in 800 g of methyl ethyl ketone.

EXAMPLE VIII

A test film piece 1 was prepared by applying a dispersion liquid of coating substance to a support 11 made of a paper sheet 100 μm in thickness that was laminated with a polyolefin resin to form a lamination of a coating film 12 on the support 11. The dispersion liquid was prepared by dispersing 400 g of a polyester resin and 60 g of titanium dioxide (Taipek® A-220 commercially distributed by Ishihara Sangyo Co., Ltd.) in 800 g of methyl ethyl ketone. In this instance, the polyester resin was a polymer of a telephthalic acid and ethylene oxide modified bisphenol A that had a number average molecular weight of 5000 and a glass transition temperature (Tg) of 65° C.

EXAMPLE IX

A test film piece 1 was prepared by applying a dispersion liquid of coating substance to a support 11 made of a paper sheet that was laminated with a polyolefin resin to form a lamination of a coating film 12 on the support 11. The dispersion liquid was prepared by dispersing 400 g of a polyester resin (Tafton® U-5 commercially distributed by Kao Corporation), 60 g of titanium dioxide (Taipek® A-220 commercially distributed by Ishihara Sangyo Co., Ltd.) and 23.3 g of triphenyl phosphin (TPP) (commercially distributed by Daihachi Chemical Co., Ltd.) in 800 g of methyl ethyl ketone.

The results of measurements of acoustic emissions and the presence or the absence of flexural crazing and spontaneous crazing are demonstrated in Table I as shown below. In Table I, the sign "Yes" indicates the presence of flexural crazing or spontaneous crazing, and the sign "No" indicates the absence of flexural crazing or spontaneous crazing. Further, the term "AE signal-representing deformation" means a distance of descent of the compression head 22*a* in mm at detection of a first acoustic emission. 3 regarding Example V, the indication of "over 3" for AE signal-representing deformation means that any acoustic emission was not detected even when the compression head 22*a* descended a distance of 3 mm that was a limit distance of descent of the compression head 22*a*.

Elongation after fracture is demonstrated for the test film pieces 1 of Examples IV~VI and IX. However, regarding the test film pieces 1 of Examples VII and VIII, the visual examination of elongation after fracture was not carried out because the coating films 12 were too brittle to be independently removed from the supports 11.

TABLE I

|  | AE signal-representing deformation (mm) | Spontaneous crazing | Flexural crazing | Elongation after-fracture (%) |
| --- | --- | --- | --- | --- |
| Example IV | 2.05 | No | No | 0.27 |
| Example V | Over 3.00 | No | No | 168.8 |
| Example VI | 2.17 | No | No | 12.3 |
| Example VI | 1.95 | Yes | Yes | — |
| Example VIII | 1.95 | Yes | Yes | — |
| Example IX | — | Yes | Yes | 0.21 |

As clearly turned out from the result demonstrated in Table I, in the event where the test film piece 1 causes AE signal-representing deformation greater than at least 2.05 mm, neither spontaneous clacking nor flexural crazing grows up. In light of the empirical findings, in the manufacture of, for example, electrophotographic image receiving sheets, when sorting out a coating substance, i.e. an electrophotographic image receiving material whose test film piece 1 (that is prepared by applying a dispersion liquid of the coating substance to a support 11 100 μm in thickness to form a lamination of a coating film 12 on the support 11 so that a spread of the coating substance is 15 g/m² after drying) shows an AE signal-represented deformation greater than 2 mm that is the rating standard for brittleness, an electrophotographic image receiving sheet comprising a layer of the coating substance is very unlikely to cause crazing. Accordingly, it is realized to offer reliable and quality electrophotographic image receiving sheets without performing bending test and the like.

As also clearly turned out from the result demonstrated in Table I, the test film piece 1 shows comparatively large elongation-after-fracture in the event where it produces no crazing. Specifically, the test film piece 1 that shows an AE signal represented deformation greater than 2.05 mm produces no crazing and shows elongation-after-fracture greater than 0.27%. Therefore, when sorting electrophotographic image receiving materials using both elongation-after-fracture of 0.27% and AE signal represented deformation of 2 mm as rating standards, it is realized to offer more reliable electrophotographic image receiving sheets.

It is to be understood that, although the present invention has been described with regard to various preferred embodiments thereof, various other embodiments and variants may occur to those skilled in the art, which are within the scope and spirit of the invention, and such other embodiments and variants are intended to be covered by the following claims.

What is claimed is:

1. A method of predicting brittleness of a freestanding film comprising the steps of:
   causing a test piece formed by laminating a support with a coating substance to produce deformation, the coating substance being made from a same material as the freestanding film;

detecting acoustic emissions that said coating substance produces resulting from said deformation; and rating brittleness of only said coating substance on the basis of an outcome of said detection of acoustic emissions.

2. A brittleness rating method of rating brittleness of a coating substance for an intended use as defined in claim 1, wherein said deformation is produced by applying an external load to said test film piece supported at opposite sides in a transverse direction of said test film piece at a middle between said opposite sides by compressive means.

3. A brittleness rating method of rating brittleness of a coating substance for an intended use as defined in claim 2, wherein said external load is applied to said test film piece by said compression head descending at a constant speed.

4. A brittleness rating method of rating brittleness of a coating substance for an intended use as defined in claim 1, wherein said acoustic emissions are detected by an acoustic emission sensor attached to said test film piece.

5. A brittleness rating method of rating brittleness of a coating substance for an intended use as defined in claim 1, wherein brittleness of said coating substance is rated on the basis of said deformation at said detection of a first acoustic emission.

6. A brittleness rating method of rating brittleness of a coating substance for an intended use as defined in claim 3, wherein brittleness of said coating substance is rated as qualified for an electrophotographic image receiving film in the event that a distance of-descent of said compression head is greater than 2 mm at detection of a first one of said acoustic emissions when said test film piece is supported at opposite sides separated at a distance of 50 mm in a transverse direction of said test film piece.

7. A brittleness rating device for rating brittleness of a coating substance for an intended use which uses a test film piece prepared by laminating a support with said coating substance, said brittleness rating equipment comprising:

deforming means for causing said test film piece to produce deformation by applying an external load to said test film piece supported at opposite sides in a transverse direction of said test film piece at a middle between said opposite sides by compressive means;

acoustic emission detecting means for detecting acoustic emissions that said coating substance produces resulting from said deformation of said test film piece, said acoustic emission detecting means being detachably attached to said test film piece; and rating means for rating brittleness of only said coating substance on the basis of an output from said acoustic emission detecting means.

8. A brittleness rating device for rating brittleness of a coating substance for an intended use as defined in claim 7, wherein said deforming means comprises a compressive transverse test device having two supporting wedges for supporting said test film piece at opposite sides in a transverse direction of said test film piece and a compressive head for applying an external load to said test film piece at a middle between said opposite sides.

9. A brittleness rating device for rating brittleness of a coating substance for an intended use as defined in claim 8, wherein said compressive head descends at a constant speed.

10. A method of predicting brittleness of a freestanding film comprising the steps of:

creating a laminated test piece by applying to a support piece a coating substance that can be used to produce the freestanding film;

deforming the laminated test piece at a known rate;

detecting acoustic emissions generated by the laminated test piece due to the deformation; and predicting a brittleness rating of the freestanding film based on the acoustic emissions from the laminated test piece.

11. The method of predicting brittleness of claim 10, wherein the deforming step comprises:

providing support to one face of the test piece at opposite ends in a transverse direction; and applying an external load to an opposing face of the test piece between said opposite ends by a compression head.

12. The method of predicting brittleness of claim 11, wherein said external load is applied by causing the compression head to descend at a constant speed.

13. The method of predicting brittleness of claim 10, wherein said acoustic emissions are detected by an acoustic emission sensor attached to said test piece.

14. The method of predicting brittleness of claim 10, wherein the predicted brittleness of said freestanding film is provided based on an extent of said deformation at the time of said detection of a first acoustic emission.

15. The method of predicting brittleness of claim 12, wherein the predicted brittleness of the freestanding film is rated as qualified for an electrophotographic image receiving film in the event that a distance of descent of said compression head is greater than 2 mm upon detection of a first one of said acoustic emissions when said test piece is supported at opposite sides separated at a distance of 50 mm in a transverse direction of said test piece.

16. The method of predicting brittleness of claim 11, wherein the face to which the support is provided is the coating substance, and the face to which compression head is applied is the support piece.

* * * * *